United States Patent
Daidoji et al.

(10) Patent No.: US 10,856,731 B2
(45) Date of Patent: Dec. 8, 2020

(54) ILLUMINATION UNIT AND ENDOSCOPE (71) Applicant: OLYMPUS CORPORATION, Tokyo (JP)

(72) Inventors: Bakusui Daidoji, Hachioji (JP); Takeshi Ito, Hino (JP); Satoshi Ohara, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 562 days.

(21) Appl. No.: 15/678,738

(22) Filed: Aug. 16, 2017

(65) Prior Publication Data

US 2017/0340195 A1 Nov. 30, 2017

Related U.S. Application Data (63) Continuation of application No. PCT/JP2015/054815, filed on Feb. 20, 2015.

(51) Int. Cl.
| | |
|---|---|
| *A61B 13/00* | (2006.01) |
| *A61B 1/32* | (2006.01) |
| *A61C 1/00* | (2006.01) |
| *A61B 1/07* | (2006.01) |
| *B29D 11/00* | (2006.01) |
| *F21V 8/00* | (2006.01) |
| *G02B 6/24* | (2006.01) |
| *A61B 1/00* | (2006.01) |

(Continued)

(52) U.S. Cl.
CPC .............. *A61B 1/07* (2013.01); *A61B 1/0011* (2013.01); *A61B 1/00126* (2013.01); *A61B 1/012* (2013.01); *A61B 1/04* (2013.01); *A61B 1/063* (2013.01); *A61B 1/0638* (2013.01); *A61B 1/0669* (2013.01); *B29D 11/00663* (2013.01); *G02B 5/0242* (2013.01); *G02B 5/0278* (2013.01); *G02B 6/0008* (2013.01); *G02B 6/241* (2013.01); *G02B 23/2469* (2013.01); *G02B 23/2476* (2013.01); *B29D 11/00798* (2013.01)

(58) Field of Classification Search
CPC ............ A61B 13/00; A61B 1/32; A61C 1/088
USPC ........................................................ 385/117
See application file for complete search history.

(56) References Cited

U.S. PATENT DOCUMENTS 6,849,308 B1 * 2/2005 Speakman ................ G03F 7/16
  427/422
7,142,758 B1 * 11/2006 Herz ...................... B82Y 20/00
  385/125

(Continued)

FOREIGN PATENT DOCUMENTS

| CN | 101027520 A | 8/2007 |
| CN | 103533879 A | 1/2014 |

(Continued)

OTHER PUBLICATIONS

International Search Report dated May 19, 2015 issued in PCT/JP2015/054815.

(Continued)

*Primary Examiner* — Kaveh C Kianni
(74) *Attorney, Agent, or Firm* — Scully, Scott, Murphy & Presser, P.C.

(57) ABSTRACT

An illumination unit includes a light guide and a light converter. Wettability which a distal end side surface of the light guide has for an enclosing member of the light converter is lower than wettability which a distal end face has for the enclosing member.

21 Claims, 7 Drawing Sheets (51) Int. Cl.
*A61B 1/012* (2006.01)
*A61B 1/04* (2006.01)
*A61B 1/06* (2006.01)
*G02B 5/02* (2006.01)
*G02B 23/24* (2006.01)

(56) References Cited

U.S. PATENT DOCUMENTS

| | | | | |
|---|---|---|---|---|
| 8,805,141 B2* | 8/2014 | Fewkes | ............... | G02B 6/001 385/100 |
| 2004/0109659 A1* | 6/2004 | Aylward | ............... | G02B 6/08 385/133 |
| 2004/0151466 A1* | 8/2004 | Crossman-Bosworth | ............... | G02B 6/25 385/140 |
| 2004/0165824 A1* | 8/2004 | Kaneko | ............... | G02B 6/32 385/33 |
| 2004/0170437 A1* | 9/2004 | Hasegawa | ......... | C03B 37/02781 398/148 |
| 2008/0089089 A1* | 4/2008 | Hama | ............... | G02B 6/4206 362/574 |
| 2009/0032983 A1* | 2/2009 | Bookbinder | ...... | C03B 37/02781 264/1.24 |
| 2009/0296193 A1* | 12/2009 | Bita | ............... | G02B 6/005 359/291 |
| 2009/0322677 A1* | 12/2009 | Lee | ............... | G06F 3/0421 345/158 |
| 2011/0227487 A1* | 9/2011 | Nichol | ............... | G02B 6/0068 315/158 |
| 2011/0273906 A1* | 11/2011 | Nichol | ............... | G02B 6/0088 362/607 |
| 2011/0277361 A1* | 11/2011 | Nichol | ............... | G02B 6/0068 40/541 |
| 2012/0056081 A1* | 3/2012 | Kozodoy | ............... | F24S 23/00 250/227.25 |
| 2013/0155723 A1* | 6/2013 | Coleman | ............... | G02B 6/0018 362/621 |
| 2014/0009592 A1 | 1/2014 | Ishida | | |
| 2014/0049983 A1* | 2/2014 | Nichol | ............... | G02B 6/0028 362/610 |
| 2014/0140091 A1* | 5/2014 | Vasylyev | ............... | G02B 6/0045 362/606 |
| 2015/0226902 A1* | 8/2015 | Ballard | ............... | G02B 6/0055 362/612 |

FOREIGN PATENT DOCUMENTS

| | | |
|---|---|---|
| JP | 2002-326884 A | 11/2002 |
| JP | 2004-240361 A | 8/2004 |
| JP | 2011-248022 A | 12/2011 |
| JP | 2015-000169 A | 1/2015 |
| WO | WO 2006/038502 A1 | 4/2006 |
| WO | WO 2013/132681 A1 | 9/2013 |

OTHER PUBLICATIONS

Japanese Office Action dated Apr. 24, 2018 in Japanese Patent Application No. 2017-500244.
Chinese Office Action dated Feb. 27, 2019 in Chinese Patent Application No. 201580076474.7.
English translation of International Preliminary Report on Patentability dated Aug. 31, 2017 together with the Written Opinion received in related International Application No. PCT/JP2015/054815.

* cited by examiner

ILLUMINATION UNIT AND ENDOSCOPE

CROSS-REFERENCE TO RELATED APPLICATIONS

This application is a Continuation Application of PCT Application No. PCT/JP2015/054815, filed Feb. 20, 2015, the entire contents of all of which are incorporated herein by reference.

BACKGROUND OF THE INVENTION

1. Field of the Invention

The present invention relates to an illumination unit and an endoscope.

2. Description of the Related Art

At the present time, for example in the medical field, illumination units which use laser light guided by an optical fiber are under development.

For example, in the illumination unit disclosed in Jpn. Pat. Appln. KOKAI Publication No. 2011-248022, an ellipsoidal diffusion body is provided at the distal end face of an optical fiber in order that light can radiate in a wide range.

BRIEF SUMMARY OF THE INVENTION

An illumination unit according to one aspect of the present invention includes: a light guide including a core which guides light, and a clad provided on the outer circumference of the core and having a refraction index smaller than the refraction index of the core; and a light converter arranged at the distal end face of the light guide and emitting illumination light obtained by converting the optical characteristics of the light guided by the light guide. Wettability which the distal end side surface of the light guide has for an enclosing member of the light converter is lower than the wettability which the distal end face of the core has for the enclosing member.

An endoscope according to one aspect of the present invention includes: an illumination unit described above; an imaging unit which images an observation target; and a holder provided at the distal end portion of an insertion portion. The holder includes a first hole into which the distal end portion of the light guide is inserted and which is a through hole penetrating the holder in the axial direction of the holder. The distal end face of the light guide is located rearward of an opening end portion of the first hole, and the distal end face of the light converter is located in same plane as the opening end portion or rearward of the opening end portion.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

Figure 1:
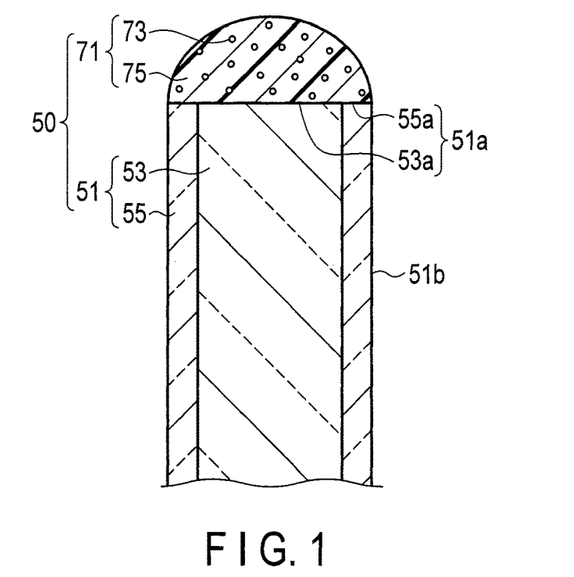
FIG. 1 is a schematic diagram showing a distal end portion of an illumination unit according to the first embodiment of the present invention.

Embodiments of the present invention will be described in detail with reference to the accompanying drawings. In FIG. 1, illustration of both a wettability reducing portion 57 and a wettability improving portion 59 is omitted. Likewise, in some of the Figures, illustration of some members is omitted for the sake of easy understanding of the structure.

First Embodiment

[Configuration]

The first embodiment will be described with reference to FIGS. 1, 2A, 2B, 3, 4A, 4B, 4C, 4D, 4E and 5.

[Configuration 1 of Illumination Unit 50]

As shown in FIG. 1, an illumination unit 50 of an illumination device includes a light guide (light guide member) 51 which guides light such as laser light, and a light converter (light conversion member) 71 arranged on a distal end face 51a of the light guide 51 and emitting illumination light obtained by converting the optical characteristics of the light guided by the light guide 51.

[Light Guide 51]

An outer diameter of the light guide 51 shown in FIG. 1 is, for example, in the range of several dozen μm to several hundred μm. The light guide 51 is, for example, an optical fiber serving as a multi-mode fiber. The material of the light guide 51 is, for example, quartz glass, a plastic or a resin. The light guide 51 is a rod-shaped member. The distal end face 51a is perpendicular to a central axis of the light guide 51, and a side surface of the light guide 51 is parallel to the central axis of the light guide 51.

As shown in FIG. 1, the light guide 51 includes a core (core portion) 53 which guides light, and a clad (clad portion) 55 provided on an outer circumference of the core 53 and having a refraction index smaller than a refraction index of the core 53.

[Light Converter 71]

The light converter 71 of the present embodiment shown in FIG. 1 functions, for example, as a light distribution converter (light distribution conversion member) which converts the light distribution of emitting light. For this reason, the light converter 71 includes a large number of diffusion particles 73 which diffuse the light emitted from the core 53, and an enclosing member 75 which encloses the diffusion particles 73 in a dispersed state. In other words, the diffusion particles 73 are dispersed inside the enclosing member 75 and sealed by the enclosing member 75.

The diffusion particles 73 are fine particles of a metal or a metal compound. The diffusion particles 73 are made of, for example, alumina or titanium oxide.

The reflectance which the diffusion particles 73 have for light is desirably 80% or higher, more desirably 90% or higher. Owing to this feature, when the light converter 71 functions as a light distribution converter, the diffusion particles 73 absorb a small amount of light and can convert input light into illumination light with high efficiency, and heat generation can be suppressed during the conversion. A distal end portion of the light guide 51 and the light converter 71, which constitute a distal end portion of the illumination unit 50, are provided in a distal end hard portion 21 (see FIGS. 7A and 7B), which is a distal end portion of an insertion portion 20 arranged in an endoscope 10. The heat generated from the light converter 71 is absorbed by the distal end hard portion 21, and the distal end hard portion 21 generates heat. Heat has adverse effects on the distal end hard portion 21 and a lumen into which the insertion portion 20 is inserted. Since the heat generation is suppressed, the adverse effects on the distal end hard portion 21 and the lumen can be reduced.

The refraction index of the diffusion particles 73 is larger than the refraction index of the enclosing member 75; desirably, it is 1.5 or more. Owing to this, the diffusion particles 73 can provide improved light diffusion property.

A diameter of each diffusion particle 73 is, for example, several hundred nm to several μm, and is determined based on the wavelength of the light and a diameter of the core 53. The light is scattered by the diffusion particles 73, each having a diameter determined based on the wavelength of the light and the diameter of the core 53, in the form of Mie scattering in which the light scatters more in the front direction than in the rear direction, or in the form of geometrical scattering. The "front" is intended to mean a direction in which illumination light is emitted. The "rear" is opposite to "front" and is intended to mean a direction opposite to the direction in which the illumination light is emitted.

To be specific, the diameter of a diffusion particle 73 is ⅕ or more of the shortest wavelength, and is ⅕ or less of the diameter of the core 53.

The light distribution angle of the light converter 71 is controlled, for example, in accordance with the concentration of the diffusion particles 73 in the enclosing member 75, the thickness of the light conversion element 71 and the like.

The enclosing member 75 is a transparent silicone-based resin or a transparent epoxy-based resin.

[Wettability Which Light Guide 51 has for Light Converter 71]

Figure 2A:
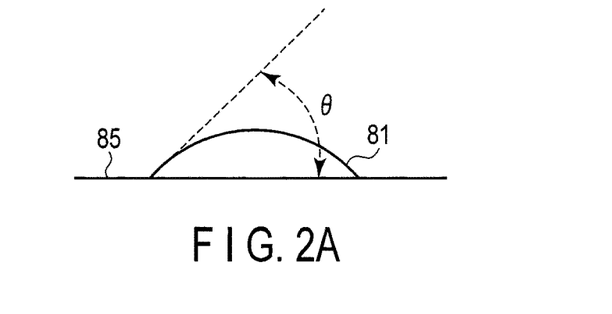
FIG. 2A is an explanatory diagram illustrating the wettability which the surface of a solid has for a liquid.
Figure 2B:
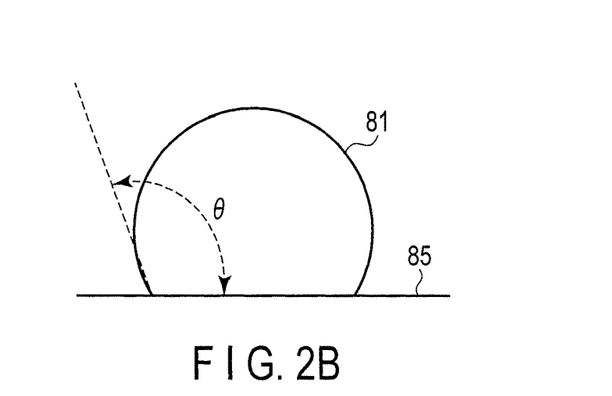
FIG. 2B is an explanatory diagram illustrating the wettability which the surface of a solid has for a liquid.

In general, wettability which a surface of a solid 83 has for a liquid 81 is defined by the contact angle θ of the liquid 81 with reference to the solid 83, as shown in FIGS. 2A and 2B. The contact angle θ is in the range of 0 to 180 degrees. Where the contact angle θ is narrow (for example, less than 90 degrees, as in FIG. 2A), the wettability is high. Where the contact angle θ is wide (for example, more than 90 degrees, as in FIG. 2B), the wettability is low.

As shown in FIG. 1, the distal end face 51a includes a distal end face of the core 53 (hereinafter referred to as a core distal end face 53a) and a distal end face of the clad 55 (hereinafter referred to as a clad distal end face 55a). The side surface of the distal end portion of the light guide 51 (hereinafter referred to as a distal end side surface 51b) is a distal end side surface of the clad 55, so that the distal end side surface 51b is continuous with the distal end face 51a, more specifically, with the clad distal end face 55a. In the present embodiment, wettability which the distal end side surface 51b has for the enclosing member 75 is lower than wettability which the core distal end face 53a has for the enclosing member 75. In the present embodiment, the wettability which the distal end side surface 51b has for the enclosing member 75 is lower than wettability which the clad distal end face 55a has for the enclosing member 75. That is, in the present embodiment, the wettability which the distal end side surface 51b has for the enclosing member 75 is lower than wettability which the distal end face 51a has for the enclosing member 75.

Figure 3:
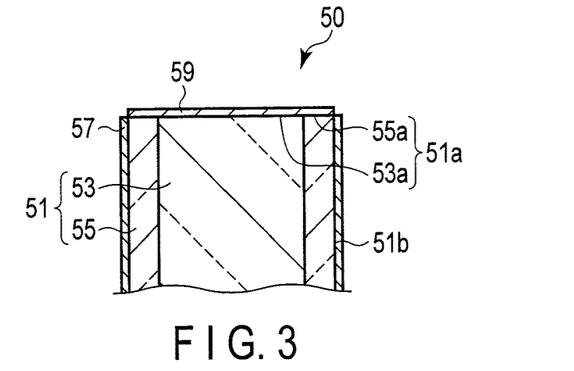
FIG. 3 illustrates a wettability reducing portion and a wettability improving portion.
Figure 4A:
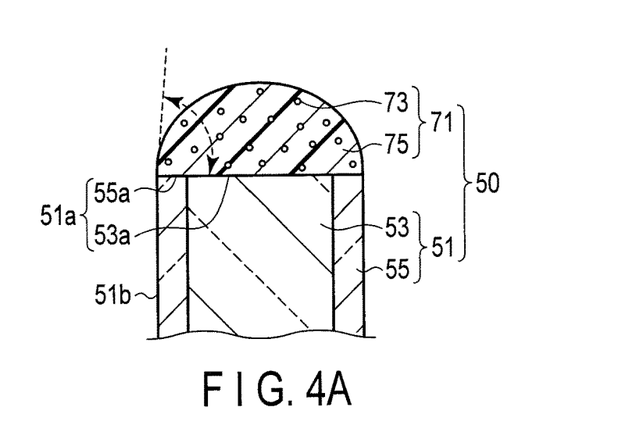
FIG. 4A illustrates how a light guide and a light converter are in contact with each other.
Figure 4B:
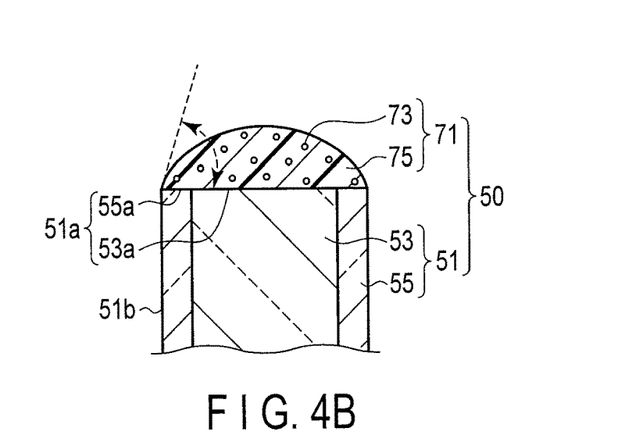
FIG. 4B illustrates how a light guide and a light converter are in contact with each other.
Figure 4C:
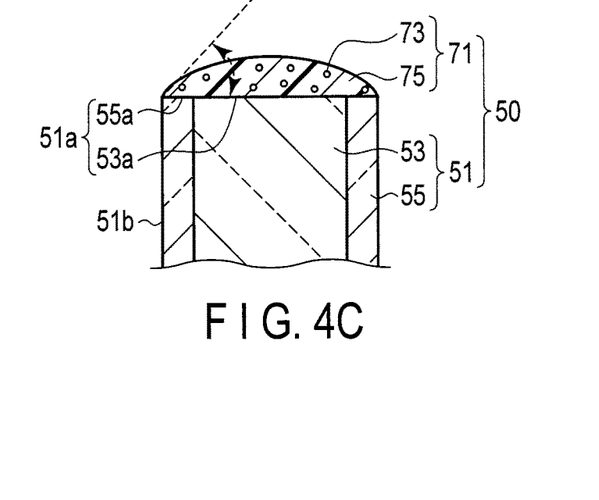
FIG. 4C illustrates how a light guide and a light converter are in contact with each other.
Figure 4D:
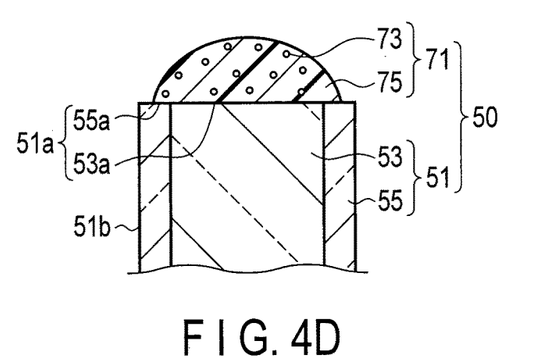
FIG. 4D illustrates how a light guide and a light converter are in contact with each other.
Figure 4E:
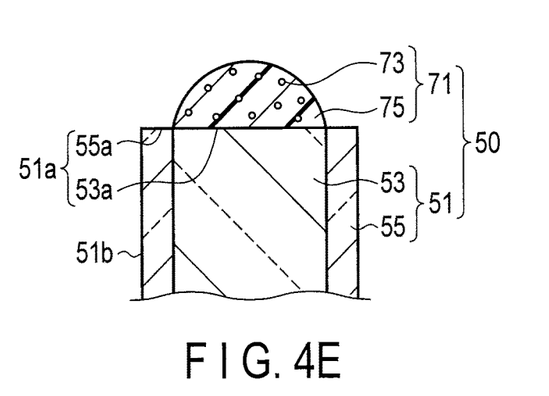
FIG. 4E illustrates how a light guide and a light converter are in contact with each other.

To provide such a wettability difference, the light guide 51 of the present embodiment includes at least one of (i) a wettability reducing portion 57 which reduces the wettability that the distal end side surface has for the enclosing member 75 and (ii) a wettability improving portion 59 which improves the wettability of the distal end face 51a, as shown in FIG. 3. The wettability reducing portion 57 is provided on the distal end side surface 51b, and the wettability improving portion 59 is provided on the distal end face 51a.

[Wettability Reducing Portion 57]

As shown in FIG. 3, the wettability reducing portion 57 covers, for example, the distal end side surface 51b of the light guide 51. In this case, wettability which the wettability reducing portion 57 has for the enclosing member 75 is lower than the wettability which the core distal end face 53a has for the enclosing member 75 and the wettability which the clad distal end face 55a has for the enclosing member 75. The wettability reducing portion 57 includes, for example, a fluoroplastic resin.

The wettability reducing portion 57 may be provided by changing the surface roughness of the distal end side surface 51b. For example, the surface roughness is changed by one of etching, abrasive blasting, and laser beam machining. The surface roughness is obtained by the Wenzel formula shown as formula (1).

$$\cos \theta = r \cos \theta 1 \qquad \text{formula (1)}$$

where θ is a contact angle relative to a flat surface, θ1 is a contact angle relative to a rough surface, and r is an area ratio of the rough surface to the flat surface.

Where the contact angle θ of the enclosing member 75 relative to the distal end side surface 51b in the flat state is less than 90 degrees, the wettability reducing portion 57 has a reduced surface roughness and decreases the wettability of the distal end side surface 51b.

Where the contact angle θ of the enclosing member 75 relative to the distal end side surface 51b in the flat state is greater than 90 degrees, the wettability reducing portion 57 has an increased surface roughness and decreases the wettability of the distal end side surface 51b.

Based on this, the wettability is decreased in accordance with the materials of the light guide 51 and the enclosing member 75.

The wettability reducing portion 57 may include a functional group which is provided on the distal end side surface 51b and which serves to decrease the wettability which the distal end side surface 51b has for the enclosing member 75. Where the enclosing member 75 is hydrophobic, the wettability reducing portion 57 includes a hydrophilic functional group which is provided on the distal end face 51a by irradiating the distal end side surface 51b with plasma or UV light. The functional group includes —OH, —COOH, or the like.

The process in which a light guide 51 having a wettability reducing portion 57 is formed is as follows. First, the wettability reducing portion 57 is provided on a distal end side surface 51b, and subsequently an end portion of the light guide 51 is cut in a direction perpendicular to the central axis of the light guide 51 in such a manner as to form a distal end face 51a. A light guide 51 formed in this process includes a distal end side surface 51b on which the wettability reducing portion 57 is provided, and a clear distal end face 51a on which the wettability reducing portion 57 is not provided.

The wettability reducing portion 57 is not limited to the example mentioned above, and a known technology may be used to reduce wettability.

[Wettability Improving Portion 59]

As shown in FIG. 3, the wettability improving portion 59 covers the distal end face 51a. In this case, wettability which the wettability improving portion 59 has for the enclosing member 75 is higher than the wettability which the distal end side surface 51b has for the enclosing member 75. Where the enclosing member 75 is hydrophobic, the wettability improving portion 59 includes a hydrophobic material. Where the enclosing member 75 is hydrophilic, the wettability improving portion 59 includes a hydrophilic material.

The wettability improving portion 59 may be provided by changing the surface roughness of the distal end face 51a. For example, the surface roughness is changed by one of etching, abrasive blasting, and laser beam machining. The surface roughness is obtained by the Wenzel formula shown as formula (1).

Where the contact angle θ of the enclosing member 75 relative to the distal end face 51a in the flat state is less than 90 degrees, the wettability improving portion 59 has an increased surface roughness and increases the wettability of the distal end face 51a.

Where the contact angle θ of the enclosing member 75 relative to the distal end face 51a in the flat state is greater than 90 degrees, the wettability improving portion 59 has a reduced surface roughness and increases the wettability of the distal end face 51a.

Based on this, the wettability is improved in accordance with the materials of the light guide 51 and the enclosing member 75.

The wettability improving portion 59 may include a functional group which is provided on the distal end face 51a and which serves to improve the wettability which the distal end face 51a has for the enclosing member 75. The wettability improving portion 59 may be formed, for example, of a silane coupling material.

The process in which a light guide 51 having a wettability improving portion 59 is formed is as follows. First, a distal end side surface 51b is masked, and subsequently the end portion of the light guide 51 is cut in the direction perpendicular to the central axis of the light guide 51 in such a manner as to form a distal end face 51a. Then, the wettability improving portion 59 is provided on the distal end face 51a, and the mask is removed. A light guide 51 formed in this process includes a distal end face 51a on which the wettability improving portion 59 is provided, and a clear distal end side surface 51b on which the wettability improving portion 59 is not provided.

The wettability improving portion 59 is not limited to the example mentioned above, and a known technology may be used to improve wettability.

[Others]

The core 53 or the clad 55 may be formed of materials such that wettability which the clad 55 has for the enclosing member 75 can be lower than wettability which the core 53 has for the enclosing member 75. The clad 55 includes, for example, a fluoroplastic resin.

[Contact State Between Light Guide 51 and Light Converter 71]

As shown in FIGS. 1, 4A, 4B, 4C, 4D and 4E, the light converter 71 is adhered only to the distal end face 51a by means of the enclosing member 75. A contact region where the light converter 71 is in contact with the distal end face 51a includes the core distal end face 53a. An outer diameter of the contact region is substantially equal to an outer diameter of the light guide 51 (clad 55), or is smaller than the outer diameter of the light guide 51 (clad 55). The light converter 71 is shaped like a dome, for example. The contact angle θ of the light converter 71 relative to the distal end face 51a is not more than 90 degrees. A maximal outer diameter of the light converter 71 is substantially equal to the outer diameter of the light guide 51 (clad 55), or is smaller than the outer diameter of the light guide 51 (clad 55). The contact region and the light converter 71 are inside a projection area of the distal end face 51a.

The outer diameter of the contact region was described as being substantially equal to the outer diameter of the light guide 51 (clad 55). This is intended to mean that the outer diameter of the contact region may be slightly larger than the outer diameter of the clad 55 and the contact region may protrude from the clad 55, due to manufacturing variations of the illumination unit 50. In other words, the outer diameter of the contact region may be slightly larger than the outer diameter of the light guide 51, and the contact region may protrude from the light guide 51. Put another way, even if the light converter 71 includes a small portion protruding from the outer diameter of the clad 55, due to the manufacturing variations of the illumination unit 50, this is included in the case where the outer diameter of the contact region is substantially equal to the outer diameter of the clad 55 and is therefore regarded as being within the present invention.

[Configuration 2 of Illumination Unit 50]

Figure 5:
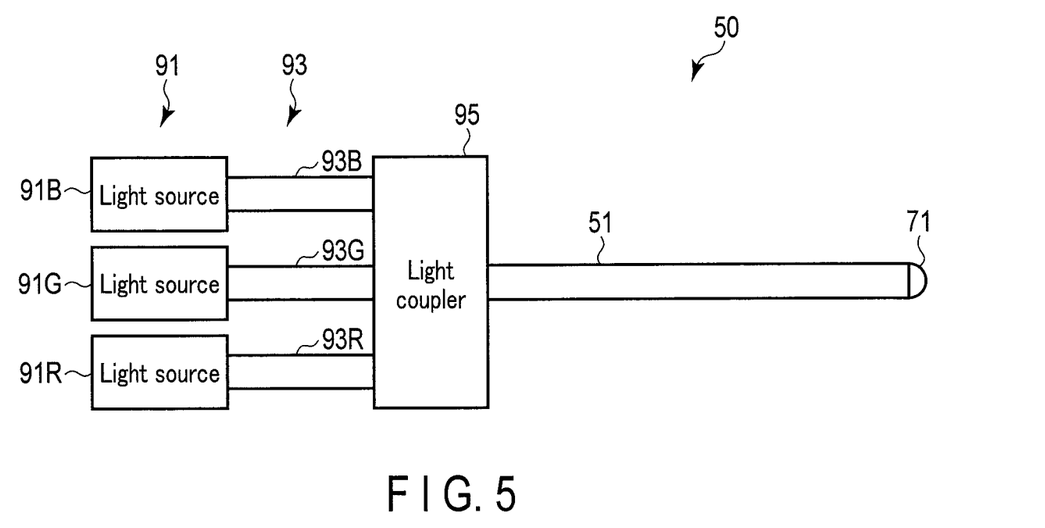
FIG. 5 is a schematic diagram illustrating an illumination unit.

As shown in FIG. 5, the illumination unit 50 includes a light source unit 91, a light guide unit 93 and a light coupler (light coupling portion) 95.

The light source unit 91 shown in FIG. 5 emits a laser light beam having one wavelength or laser light beams having different wavelengths. The light source unit 91 includes a light source 91B, a light source 91G and a light source 91R.

The light source 91B includes a laser diode for emitting blue laser light. The wavelength of the laser light is 445 nm, for example.

The light source 91G includes a laser diode for emitting green laser light. The wavelength of the laser light is 532 nm, for example.

The light source 91R includes a laser diode for emitting red laser light. The wavelength of the laser light is 635 nm, for example.

Where the light source unit 91 emits laser light beam having one wavelength, light sources 91B, 91G and 91R include laser diodes for emitting laser light having the same wavelength.

As shown in FIG. 5, the light guide unit 93 includes a light guide (light guide member) 93B, a light guide (light guide member) 93G and a light guide (light guide member) 93R.

The light guide 93B is optically connected to both the light source 91B and the light coupler 95 and serves to guide the laser light emitted from light source 91B to the light coupler 95.

The light guide 93G is optically connected to both the light source 91G and the light coupler 95 and serves to guide the laser light emitted from light source 91G to the light coupler 95.

The light guide 93R is optically connected to both light source 91R and the light coupler 95 and serves to guide the laser light emitted from light source 91R to the light coupler 95.

The light guide 93B includes, for example, a single multi-mode optical fiber. This holds true of the light guide 93G and the light guide 93R as well.

A condensing lens (not shown) is provided between the light source 91B and the light guide 93B. The light emitted from the light source 91B is condensed by the condensing lens and falls on light guide 93B. This holds true of the light source 91G and the light guide 93G as well, and also of the light source 91R and the light guide 93R as well.

As shown in FIG. 5, the light coupler 95 couples a plurality of laser light beams guided by the light guide 93B, the light guide 93G and the light guide 93R. Where the laser light beams have different wavelengths and are blue, green and red light beams, the light obtained by coupling them is white light, for example. The light coupler 95 is optically connected to the light guide 51, and emits the white light obtained by coupling to the light guide 51. As a result, the single light guide 51 enables white-light observation.

The light coupler 95 includes an optical fiber combiner, for example. Because of this, the illumination unit 50 is small in size and yet enables efficient coupling of light. The light coupler 95 may comprise a spatial optical system including, for example, a lens and a dichroic mirror.

The light sources that can be used are not limited to those described above. Where four or more light sources are used, white-light observation which uses white light having high color rendering property can be carried out. Where a light source emitting blue-violet light is employed together with the light source 91G, special-light observation utilizing the light absorbing property of hemoglobin is enabled. In the special-light observation, blood vessels are highlighted. Where a light source emitting far-red light is employed, observation using the far-red light is enabled. Light sources may be properly selected in accordance with the observation to be performed.

[Advantages]

When the illumination unit 50 is assembled, the light converter 71 is arranged on the distal end face 51a. At the time, the light converter 71 may flow from the distal end face 51a to the distal end side surface 51b. In the present embodiment, however, the wettability which the distal end side surface 51b has for the enclosing member 75 of the light converter 71 is lower than the wettability which the core distal end face 53a has for the enclosing member 75.

When the illumination unit 50 is assembled, the this wettability difference makes it hard for the light converter 71 to flow from the distal end face 51a to the distal end side surface 51b, and the light converter 71 is prevented from attaching to the distal end side surface 51b of the light guide 51. Since the light converter 71 is prevented from attaching to the distal end side surface 51b, in the light guide 51, the thickness of the distal end portion of the light guide 51 can be made uniform. When the distal end portion of the light guide 51 and the light converter 71, which constitute the distal end portion of the illumination unit 50, are assembled into the distal end hard portion 21, the distal end hard portion 21 is not thickened thereby. In addition, since the attachment of the light converter 71 is prevented, the distal end portions of light guides 51 are prevented from varying in thickness without reference to the designing method or manufacturing method. In other words, the distal end portions of the light guides 51 have the same thickness, without reference to the designing method or manufacturing method. As a result, the light guide 51 can be assembled easily into the distal end hard portion 21.

The wettability which the distal end side surface 51b has for the enclosing member 75 is lower than the wettability which the clad distal end face 55a has for the enclosing member 75.

Even where the light converter 71 is arranged not only on the core distal end face 53a but also on the clad distal end face 55a, the light converter 71 is hard to flow from the clad distal end face 55a to the distal end side surface 51b, and the light converter 71 is prevented from attaching to the distal end side surface 51b of the light guide 51. Since the attachment of the light converter 71 is prevented, in the light guide 51, the distal end portion of the light guide 51 can be made as uniform as possible. When the distal end portion of the illumination unit 50 is assembled into the distal end hard portion 21, the distal end hard portion 21 is not thickened thereby.

The light guide 51 includes a wettability reducing portion 57 provided on the distal end side surface 51b and serving to reduce the wettability which the distal end side surface 51b has for the enclosing member 75.

Because of this, the wettability which the distal end side surface 51b has for the enclosing member 75 can be reliably reduced to be lower than the wettability which the distal end face 51a has for the enclosing member 75.

The light guide 51 includes a wettability improving portion 59 provided on the distal end face 51a and serving to improve the wettability of the distal end face 51a.

Because of this, the wettability which the distal end face 51a has for the enclosing member 75 can be reliably improved to be higher than the wettability which the distal end side surface 51b has for the enclosing member 75. Since the wettability improving portion 59 has direct effects on the light converter 71, the light converter 71 is prevented from flowing from the distal end face 51a to the distal end side surface 51b.

The wettability which the clad 55 has for the enclosing member 75 may be lower than the wettability which the core 53 has for the enclosing member 75.

Unlike the case where the wettability reducing portion 57 covers the distal end side surface 51b, the wettability reducing portion 57 need not be provided, with the result that the light guide 51 can be made thin. It should be noted that the outer diameter of the clad 55 of the light guide 51 serves as the outer diameter of the illumination unit 50, and the illumination unit 50 can be thin. Since the illumination unit 50 is thin, the distal end portion of the illumination unit 50 can be easily incorporated into the distal end hard portion 21. When the distal end portion of the illumination unit 50 is incorporated into the distal end hard portion 21, the outer diameter of the clad 55 can be used as a standard for incorporation. As a result, the distal end portion of the illumination unit 50 can be easily incorporated into the distal end hard portion 21. It should be noted that the wettability reducing portion 57 and the wettability improving portion 57 can be omitted. In this case, the operation for assembling the wettability reducing portion 57 and the wettability improving portion 59 does not have to be performed.

The contact region where the light converter 71 is in contact with the distal end face 51a includes the core distal end face 53a, and the outer diameter of the contact region is substantially equal to the outer diameter of the light guide 51 (clad 55), or is smaller than the outer diameter of the light guide 51 (clad 55). The light converter 71 is shaped like a dome, for example. The contact angle θ of the light converter 71 relative to the distal end face 51a is not more than 90 degrees.

Therefore, a fixing member with which to fix the light converter 71 to the light guide 51 is not required, and the illumination unit 50 is thin, accordingly. Since the illumination unit 50 is thin, the distal end portion of the illumination unit 50 can be easily incorporated into the distal end hard portion 21. When the distal end portion of the illumination unit 50 is incorporated into the distal end hard portion 21, the outer diameter of the clad 55 can be used as a standard for incorporation. As a result, the distal end portion of the illumination unit 50 can be easily incorporated into the distal end hard portion 21. Since the light converter 71 is shaped like a dome, light is refracted at the interface between the light converter 71 and the air and can be distributed in a wide range.

Light is scattered by the diffusion particles 73 in the form of Mie scattering or geometrical scattering.

Therefore, laser light can scatter efficiently in the front direction, and the amount of light scattering in the rear direction can be reduced. As a result, the heat generation in the distal end hard portion 21 incorporating the distal end portion of the illumination unit 50 can be suppressed.

The diameter of a diffusion particle 73 is ⅕ or more of the shortest wavelength.

Owing to this, Mie scattering or geometrical scattering is made to occur.

The diameter of a diffusion particle 73 is ⅕ or less of the diameter of the core 53.

Owing to this, laser light can be fully scattered by the diffusion particles 73.

In connection with the present embodiment, reference was made to the wettability which the distal end side surface 51b has for the enclosing member 75. The wettability which the distal end side surface 51b has for the enclosing member 75 may be regarded as wettability which the side surface of the light guide 51 has for the enclosing member 75.

[Modification]

Figure 6:
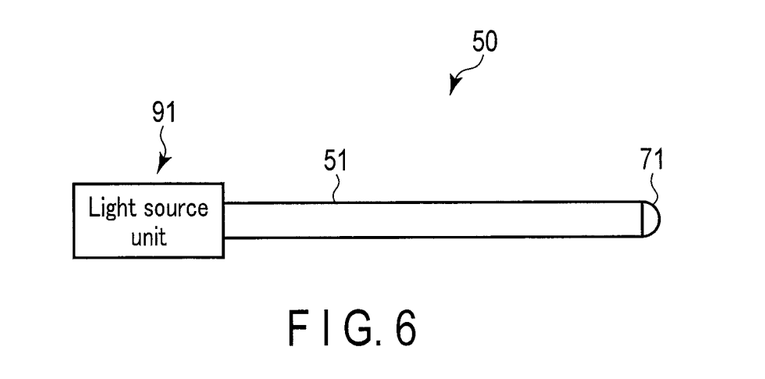
FIG. 6 illustrates a modification of the first embodiment and shows an illumination unit according to the modification.

As shown in FIG. 6, the light converter 71 may function as a wavelength converter (wavelength conversion member) which emits light of a different wavelength in response to the irradiation of light. When irradiated with laser light, the light converter 71 emits fluorescent light. The light converter 71 includes, for example, a yellow fluorescent substance which emits yellow fluorescence when irradiated with blue laser light of 445 nm. That is, the light converter 71 emits the blue laser light in a diffused manner and also emits the yellow fluorescence. As a result, the light converter 71 can emit white illumination light. The light guide 51 is connected directly to the light source unit 91.

Second Embodiment

An endoscope system 5 including an endoscope 10 provided with the illumination unit 50 of the first embodiment will be described with reference to FIGS. 7A, 7B, 8A and 8B.

Figure 8A:
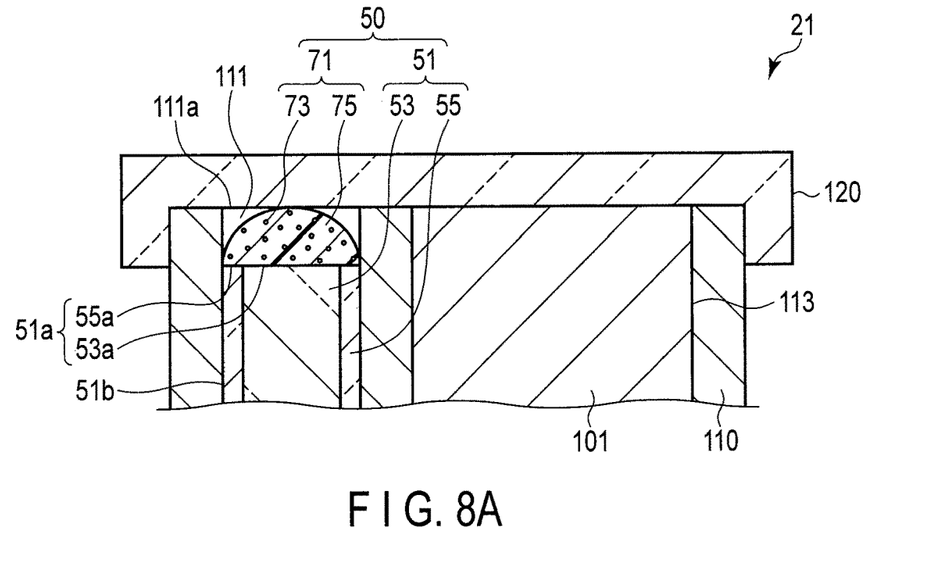
FIG. 8A illustrates the structure of a holder.

In FIG. 8A, illustration of a wettability reducing portion 57, a wettability improving portion 59, an adhesion region 115 and a non-adhesion region 117 is omitted for the sake of easy understanding of the structure.

[Endoscope System 5]

Figure 7A:
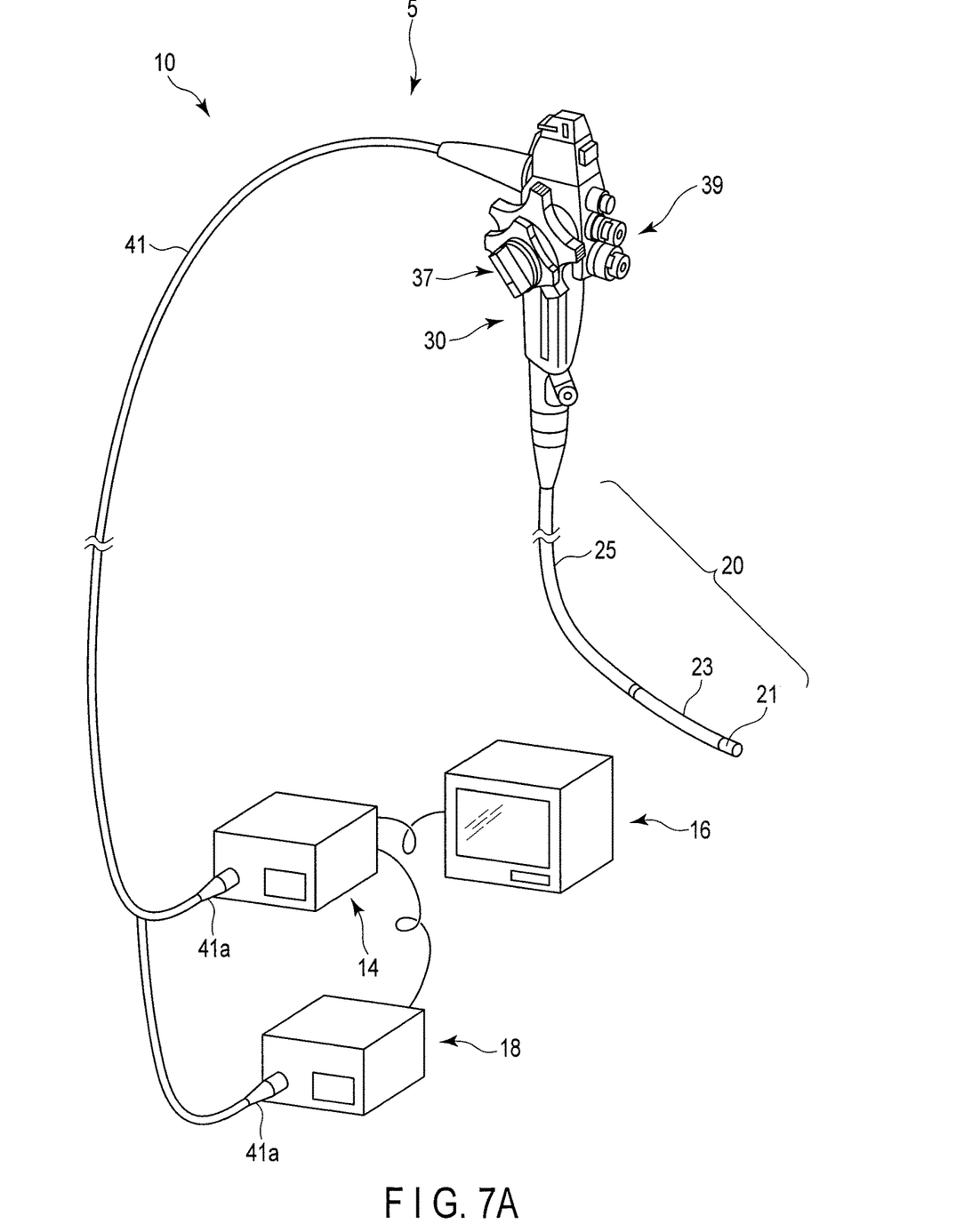
FIG. 7A illustrates the second embodiment of the present invention and is a schematic perspective view of an endoscope system including an endoscope which employs the illumination unit of the first embodiment.

As shown in FIG. 7A, the endoscope system 5 comprises, for example, an endoscope 10 which emits illumination light to an observation target and takes an image of the observation target, and a controller (control device) 14 which is removably connected to the endoscope 10. The observation target is, for example, an affected portion or a disease portion of a body cavity.

As shown in FIG. 7A, the endoscope system 5 also comprises an display (image display device) 16 (e.g., a monitor) which is connected to the controller 14 and configured to display the observation target imaged by the endoscope 10, and a light source device 18 which is removably connected to the endoscope 10 and is removably connected to the controller 14.

Figure 7B:
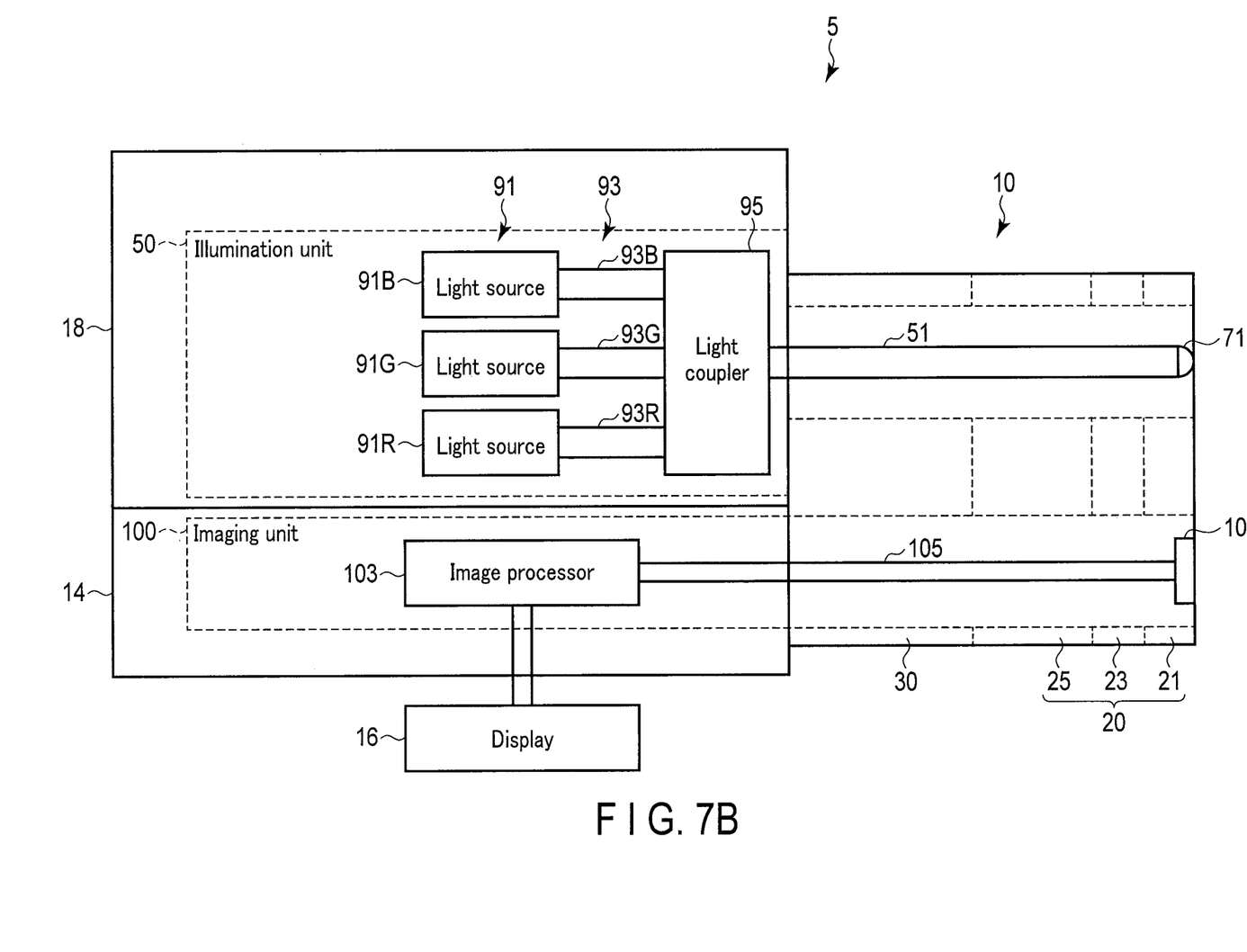
FIG. 7B illustrates the structure of the endoscope system depicted in FIG. 7A.

As shown in FIG. 7B, the endoscope system 5 further comprises an imaging unit 100 an imaging device which images the observation target. The imaging unit 100 includes an imager (imaging portion) 101 for imaging the observation target, and an image processor (image processing portion) 103 for processing images taken by the imager 101. The images taken by the imager 101 are transmitted to the image processor 103 through an imaging cable 105. The images processed by the image processor 103 are displayed on the display 16. The imager 101 is provided for the distal end hard portion 21, the image processor 103 is provided for the controller 14, and the imaging cable 105 is provided for the endoscope 10.

[Endoscope 10]

As shown in FIG. 7A, the endoscope 10 comprises the hollow elongated insertion portion 20 to be inserted into a body cavity, and a grasping portion 30 coupled to a proximal end portion of the insertion portion 20 and grasped by an operator.

As shown in FIG. 7B, the light guide 51 and the light converter 71 are incorporated in the endoscope 10.

[Insertion Portion 20]

As shown in FIG. 7A, the insertion portion 20 includes, from its distal end portion side to its proximal end portion side, a distal end hard portion 21, a bendable portion 23 and a flexible tube portion 25. A proximal end portion of the distal end hard portion 21 is coupled to a distal end portion of the bendable portion 23, and a proximal end portion of the bendable portion 23 is coupled to a distal end portion of the flexible tube portion 25.

As shown in FIG. 7B, the imager 101 which is a distal end portion of the imaging unit 100, and the distal end portion of the light guide 51 and the light converter 71 which constitute a distal end portion of the illumination unit 50 are provided in the distal end hard portion 21.

[Grasping Portion 30]

As shown in FIG. 7A, the flexible tube portion 25 extends from the grasping portion 30. The grasping portion 30 includes a bending operation portion 37 which is operated to bend the bendable portion 23, a switch portion 39 which is operated to supply air and/or water or to perform suction, and a universal cord 41 which is connected to the grasping portion 30.

[Universal Cord 41]

As shown in FIG. 7A, the universal cord 41 extends from a side surface of the grasping portion 30. An end portion of the universal cord 41 branches into two portions, and connectors 41a are provided on the respective branch ends. One of the connectors 41a is detachably attached to the controller 14, while the other connector 41a is detachably attached to the light source device 18.

[Controller 14, Display 16, and Light Source Device 18]

The controller 14 controls the endoscope 10, the display 16 and the light source device 18.

As shown in FIG. 7B, the light source device 18 includes a light source unit 91, a light guide unit 93 and a light coupler 95. [How Distal End Portion of Illumination Unit 50 is Arranged in Distal End Hard Portion 21]

As shown in FIG. 8A, the distal end hard portion 21 includes a tubular holder (holding member) 110 for holding the distal end portion of the illumination unit 50 and a cover (covering member) 120 for covering a distal end face of the holder 110.

As shown in FIG. 8A, the holder 110 includes a first hole (first hole portion) 111 into which the distal end portion of the light guide 51 is inserted. The holder 110 holds the distal end portion of the illumination unit 50 such that the distal end portion of the illumination unit 50 is located in the first hole 111. In this state, the distal end face 51a is located rearward of an opening end portion 111a of the first hole 111, and a distal end face of the light converter 71 is located in the same plane as the opening end portion 111a of the first hole 111 or rearward of the opening end portion 111a of the first hole 111. The first hole 111 is a through hole (through hole portion) penetrating the holder 110 in the axial direction thereof. The opening end portion 111a is a foremost marginal region of the first hole 111.

In the present embodiment, the distal end portion of the illumination unit 50 is inserted into the first hole 111 without the light guide 51 being held by a holder such as a ferrule. In the present embodiment, the light guide 51 is directly inserted into the first hole 111 of the light guide 51, and the clad 55 of the light guide 51 or the wettability reducing portion 57 comes into direct contact with an inner circumferential face of the first hole 111.

As shown in FIG. 8A, the holder 110 holds a distal end portion of the imaging unit 100 as well. To be more specific, the holder 110 holds the distal end portion of the illumination unit 50 and the distal end portion of the imaging unit 100, such that the distal end portion of the illumination unit 50 and the distal end portion of the imaging unit 100 are adjacent to each other, the illumination unit 50 can emit illumination light in the front direction, and the imaging unit 100 can take an image of what exists in the front direction. Therefore, the holder 110 includes a second hole (second hole portion) 113 into which the distal end portion of the imaging unit 100 is inserted. The first hole 111 and the second hole 113 are adjacent to each other such that the distal end portion of the illumination unit 50 and the distal end portion of the imaging unit 100 are adjacent to each other. The second hole 113 is a through hole (through hole portion) penetrating the holder 110 in the axial direction thereof.

The distal end portion of the illumination unit 50 is adhered to an inner circumferential face of holder 110 in the first hole 111 by means of an adhesive (not shown), and the distal end portion of the imaging unit 100 is adhered to an inner circumferential face of holder 110 in the second hole 113 by means of an adhesive (not shown). The fixing method is not limited to the adhesion, and engagement may be used.

As shown in FIG. 8A, both the distal end portion of the light guide 51 and the distal end portion of the imaging unit 100 are directly held by the single holder 110. In other words, the holder 110 for the illumination unit 50 and the holder 110 for the imaging unit 100 are not different; the holder 110 for the illumination unit 50 and the holder 110 for the imaging unit 100 are the same. One holder 110 is shared by the illumination unit 50 and the imaging unit 100.

Because of the above-mentioned arrangement of the distal end portion of the illumination unit 50 in the first hole 111 and of the use of the single holder 110, only one holder 110, functioning as a fixing member for fixing the illumination unit 50 and the imaging unit 100, is provided at the distal end portion of the insertion portion 20 of the endoscope 10. With this structure, the number of parts required can be reduced, and the insertion portion 20 can be made thin.

The holder 110 functions as a frame member. The holder 110 is formed of a metallic material, for example.

The cover 120 is located in front of the distal end portion of the illumination unit 50 and the distal end portion of the imaging unit 100. The cover 120 is in tight contact with the distal end face and side surface of the holder 110. The light emitted from the illumination unit 50 can pass through the cover 120, and the light reflected by an observation target can pass through the cover 120 for imaging by the imaging unit 100. As can be seen from this, the cover 120 is transparent.

The distal end hard portion 21 includes a medium member (not shown) which is provided between the enclosing member 75 and the cover 120 and has a refraction index lower than that of the enclosing member 75. The medium member may be, for example, an air layer or a resin member having a reflection index lower than that of the enclosing member 75. The light distribution can be widened by the refraction at the interface between the light converter 71 and the medium member. Where the medium member is a resin member, it is made by first adhering the distal end portion of the illumination unit 50 to the wall of the first hole ill and then pouring resin from the opening end portion 111a of the first hole 111.

[Wettability of Inner Circumferential Face of First Hole 111]

Figure 8B:
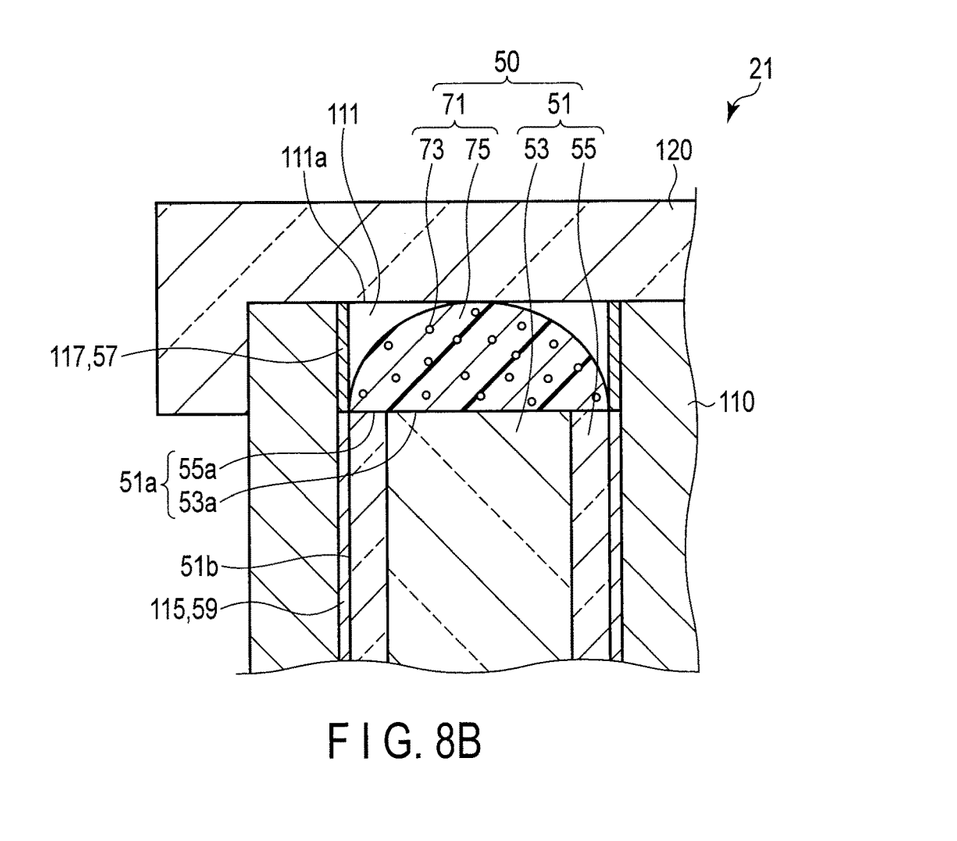
FIG. 8B illustrates an adhesion region and a non-adhesion region.

As shown in FIG. 8B, the first hole 111 includes an adhesive region 115 and a non-adhesive region 117 which are provided on an inner circumferential face of the first hole 111. The adhesive region 115 is a region to which the distal end side surface 51b of the light guide 51 is adhered by means of an adhesive. The non-adhesive region 117 is a region to which the distal end side surface 51b of the light guide is not adhered. The non-adhesive region 117 is lateral to the light converter 71. Therefore, the adhesive region 115 is located rearward of the non-adhesive region 117, and continuous with the non-adhesive region 117 in the axial direction of the light guide 51.

Wettability which the non-adhesive region 117 has for the adhesive is lower than wettability which the adhesive region 115 has for the adhesive.

If the adhesive coated on the adhesive region 115 flows to ahead of the distal end face 51a, that is, the non-adhesive region 117, the adhesive comes into contact with the light converter 71. The refraction index at the interface between the adhesive and the air is smaller than the refraction index at the interface between the light converter 71 and the air. Therefore, the illumination light may leak sideways from the portion where the adhesive is in contact with the light converter 71. As a result, the illumination efficiency may lower. In the present embodiment, however, the wettability which the non-adhesive region 117 has for the adhesive is lower than the wettability which the adhesive region 115 has for the adhesive. Owing to this, the adhesive is prevented from flowing to the non-adhesive region 117, and the illumination light is prevented from leaking sideways. As a result, the illumination efficiency is prevented from lowering.

In order to realize the feature wherein the wettability which the non-adhesive region 117 has for the adhesive is lower than the wettability which the adhesive region 115 has for the adhesive, the first hole 111 includes at least one of the wettability reducing portion 57 provided on the non-adhesive region 117 and the wettability improving portion 59 provided on the non-adhesive region 115, as shown in FIG. 8B.

The process in which the light guide 51 is arranged on the first hole 111 having the wettability reducing portion 57 is as follows. First, the distal end face of the light converter 71 is masked, subsequently the light guide 51 is arranged in the first hole 111, and then the non-adhesive region 117 is irradiated with plasma or UV light. As a result, the wettability reducing portion 57 is provided only on the non-adhesive region 117. Thereafter, the adhesive is coated on the adhesive region 115, and the light guide 51 is adhered to the first hole 111.

The process in which the wettability improving portion 59 is formed is as follows. First, the non-adhesive region 117 is masked before the light guide 51 is arranged on the first hole 111, subsequently, the wettability improving portion 59 is provided on the adhesive region 115, thereafter an adhesive is coated on the adhesive region 115, and the light guide 51 is arranged on the first hole 111 and adhered thereto.

[Advantages]

The distal end face 51a is located rearward of the opening end portion 111a of the first hole 111, and the distal end face of the light converter 71 is located in the same plane as the opening end portion 111a of the first hole 111 or rearward of the opening end portion 111a of the first hole 111.

With this structure, the distal end hard portion 21 can be assembled with ease.

Both the distal end portion of the light guide 51 and the distal end portion of the imaging unit 100 are directly held by the single holder 110.

In other words, the holder 110 functions as a member for positioning the light guide 51 and the imaging unit 100 with reference to the insertion portion 20. Therefore, the number of parts required can be reduced, and the distal end hard portion 21 can be made thin.

The light guide 51 is directly inserted into the first hole 111, and the clad 55 of the light guide 51 or the wettability reducing portion 57 comes into direct contact with the inner circumferential face of the first hole 111.

That is, the distal end portion of the illumination unit 50 is inserted into the first hole 11, without the light guide 51 being held by a ferrule or the like. That is, the light guide 51 is inserted directly into the first hole 111. With this structure, the illumination unit can be made thin, and eventually the distal end hard portion 21 can be made thin. It should be noted that the wettability for a liquid and the wettability for a resin are opposite to each other. Therefore, the wettability reducing portion 57 of the light guide 51 functions as a wettability improving portion 59 for a liquid adhesive and thus functions as an adhesion improving portion as well.

The wettability which the non-adhesive region 117 has for the adhesive is lower than the wettability which the adhesive region 115 has for the adhesive.

If the adhesive coated on the adhesive region 115 flows to ahead of the distal end face 51a of the light converter 71, that is, the non-adhesive region 117, the adhesive comes into contact with the light converter 71. The refraction index at the interface between the adhesive and the air is smaller than the refraction index at the interface between the light converter 71 and the air. Therefore, the illumination light may leak sideways from the portion where the adhesive is in contact with the light converter 71. As a result, the illumination efficiency may lower. In the present embodiment, however, the wettability of the non-adhesive region 117 is lower than the wettability of the adhesive region 115, so that the adhesive is prevented from flowing to the non-adhesive region 117. As a result, the illumination light is prevented from leaking sideways, and the illumination efficiency is prevented from lowering.

The present invention is not limited to the above-described embodiments and can be embodied in practice by modifying the structural elements without departing from the gist of the invention. In addition, various inventions can be made by properly combining the structural elements disclosed in connection with the above embodiments.

What is claimed is:

1. An illumination unit comprising:
    a light guide including a core which guides light, and a clad provided on an outer circumference of the core and having a refraction index smaller than that of the core; and
    a light converter arranged on a distal end face of the light guide and emitting illumination light obtained by converting optical characteristics of the light guided by the light guide, light converter having a curved outer face,
    wherein a first wettability which a distal end side surface of the light guide has for the light converter is lower than a second wettability which a distal end face of the core has for the the light converter,
    the light converter includes diffusion particles which diffuse the light, and
    the light guide includes a wettability reducing portion provided on the distal end side surface configured to reduce the first wettability and a wettability improving portion provided on the distal end face of the light guide configured to increase the second wettability.

2. The illumination unit according to claim 1, wherein the first wettability is lower than a third wettability which a distal end face of the clad has for the light converter.

3. The illumination unit according to claim 1, wherein the wettability reducing portion is arranged to cover the distal end side surface, and
    a wettability of the wettability reducing portion is lower than the second wettability and a third wettability which a distal end face of the clad has for the light converter.

4. The illumination unit according to claim 1, wherein
    where a contact angle θ of the light converter relative to the distal end side surface in a flat state is less than 90 degrees, the wettability reducing portion comprises applying a deceased surface roughness to the distal end side surface, and
    where the contact angle θ of the light converter relative to the distal end side surface in the flat state is greater than 90 degrees, the wettability reducing portion comprises applying an increased surface roughness to the distal end side surface.

5. The illumination unit according to claim 1, wherein the wettability reducing portion includes one or more of surface treatments and surface materials provided on the distal end side surface to reduce the first wettability.

6. The illumination unit according to claim 1, wherein the wettability improving portion is arranged to cover the distal end side surface, and
a wettability of the wettability improving portion is higher than the first wettability.

7. The illumination unit according to claim 1, wherein
where a contact angle θ of the light converter relative to the distal end face of the light guide in a flat state is less than 90 degrees, the wettability improving portion comprises applying an increased surface roughness to the distal end face of the light guide, and
where the contact angle θ of the light converter relative to the distal end face of the light guide in the flat state is greater than 90 degrees, the wettability improving portion comprises applying a reduced surface roughness to the distal end face of the light guide.

8. The illumination unit according to claim 1, wherein the wettability improving portion includes one or more of surface treatments and surface materials provided on the distal end face of the light guide increase the second wettability.

9. The illumination unit according to claim 1, wherein a third wettability which the clad has for the light converter is lower than the second wettability.

10. The illumination unit according to claim 1, wherein a contact region where the light converter is in contact with the distal end face of the light guide includes the distal end face of the core, and an outer diameter of the contact region is substantially equal to an outer diameter of the light guide or is smaller than the outer diameter of the light guide.

11. The illumination unit according to claim 1, wherein the light converter is shaped like a dome, and
a contact angle θ of the light converter relative to the distal end face of the light guide is not more than 90 degrees.

12. The illumination unit according to claim 1, wherein the light guide is configured to convert a light distribution of the light.

13. The illumination unit according to claim 1, wherein the light converter encloses the diffusion particles such that the diffusion particles are dispersed away from each other.

14. The illumination unit according to claim 1, wherein
the diffusion particles have a diameter determined based on a wavelength of the light and a diameter of the core, and
the light, which is guided, is scattered by the diffusion particles, each having the diameter determined based on the wavelength of the light and the diameter of the core, in a form of Mie scattering in which the light scatters more in a front direction than in a rear direction, or in a form of geometrical scattering.

15. The illumination unit according to claim 14, wherein the diameter of each diffusion particle is ⅕ or more of a shortest wavelength, and is ⅕ or less of the diameter of the core.

16. The illumination unit according to claim 1, wherein the light converter functions as a wavelength converter which emits light of a different wavelength in response to irradiation of light.

17. The illumination unit according to claim 1, further comprising:
a light source unit which emits a laser light beam having one wavelength or laser light beams having different wavelengths.

18. The illumination unit according to claim 17, further comprising:
a light coupler which couples the laser light beams having different wavelengths.

19. An endoscope comprising:
an illumination unit according to claim 1;
an imaging unit which images an observation target; and
a holder provided at a distal end portion of an insertion portion,
wherein the holder includes a first hole into which a distal end portion of the light guide is inserted and which is a through hole penetrating the holder in an axial direction of the holder,
the distal end face of the light guide is located rearward of an opening end portion of the first hole, and a distal end face of the light converter is located in same plane as the opening end portion or rearward of the opening end portion.

20. The endoscope according to claim 19, wherein the holder includes a second hole into which a distal end portion of the imaging unit is inserted and which is a through hole penetrating the holder in the axial direction of the holder,
the first hole and the second hole are adjacent to each other such that the distal end portion of the illumination unit and the distal end portion of the imaging unit are adjacent to each other, and
the holder directly holds both the distal end portion of the light guide and the distal end portion of the imaging unit.

21. The endoscope according to claim 20, wherein the first hole includes
an adhesive region which is provided on an inner circumferential face of the first hole and to which the distal end side surface is adhered by means of an adhesive, and
a non-adhesive region which is provided on the inner circumferential face of the first hole and to which the distal end side surface is not adhered,
wettability which the non-adhesive region has for the adhesive is lower than wettability which the adhesive region has for the adhesive.

* * * * *